(12) United States Patent
Sookraj

(10) Patent No.: US 9,719,037 B2
(45) Date of Patent: Aug. 1, 2017

(54) METHODS FOR PRODUCTION OF TEREPHTHALIC ACID FROM ETHYLENE OXIDE

(71) Applicant: NOVOMER, INC., Waltham, MA (US)

(72) Inventor: Sadesh H. Sookraj, Waltham (ZA)

(73) Assignee: Novomer, Inc., Waltham, MA (US)

(*) Notice: Subject to any disclaimer, the term of this patent is extended or adjusted under 35 U.S.C. 154(b) by 0 days.

(21) Appl. No.: 15/197,838

(22) Filed: Jun. 30, 2016

(65) Prior Publication Data

US 2017/0001940 A1 Jan. 5, 2017

Related U.S. Application Data

(60) Provisional application No. 62/187,329, filed on Jul. 1, 2015.

(51) Int. Cl.

| | | |
|---|---|---|
| *C07C 51/14* | (2006.01) |
| *C10J 3/72* | (2006.01) |
| *C07D 301/03* | (2006.01) |
| *C07D 307/60* | (2006.01) |
| *C07D 493/18* | (2006.01) |
| *C07D 307/89* | (2006.01) |
| *C07C 1/24* | (2006.01) |
| *C07C 51/41* | (2006.01) |

(52) U.S. Cl.
CPC ........ *C10J 3/72* (2013.01); *C07C 1/24* (2013.01); *C07C 51/416* (2013.01); *C07D 301/03* (2013.01); *C07D 307/60* (2013.01); *C07D 307/89* (2013.01); *C07D 493/18* (2013.01); *C10J 2300/0916* (2013.01)

(58) Field of Classification Search
None
See application file for complete search history.

(56) References Cited

U.S. PATENT DOCUMENTS

| | | |
|---|---|---|
| 3,885,155 A | 5/1975 | Anbar |
| 4,230,885 A | 10/1980 | Wu |
| 4,427,884 A | 1/1984 | Anbar et al. |
| 4,973,841 A | 11/1990 | Purser |
| 5,438,194 A | 8/1995 | Koudijs et al. |

(Continued)

FOREIGN PATENT DOCUMENTS

| | | |
|---|---|---|
| WO | WO 2009/155086 | 12/2009 |
| WO | WO 2010/118128 | 10/2010 |

(Continued)

OTHER PUBLICATIONS

Slowik, M. et al., "Catalytic; conversion of waste carbon monoxide to valuable chemicals & materials." Clean Technology, 2010, pp. 283-286. See p. 283; and figures 1, 2. Only pp. 283-284
Getzler Y. D. Y. L., "Catalytic carbonylation of beta-lactones to succinic anhydrides," Journal of the American Chemical Society, 2004, vol. 126, No. 22, pp. 6842-6543. See Table 1 Abstract Only.

(Continued)

*Primary Examiner* — Sudhakar Katakam
*Assistant Examiner* — Jennifer C Sawyer
(74) *Attorney, Agent, or Firm* — Spence, PC

(57) ABSTRACT

The present invention provides methods for the production of terephthalic acid and derivatives thereof using ethylene oxide, carbon monoxide and furan as feedstocks. The process is characterized by high yields and high carbon efficiency. The process can utilize 100% biobased feedstocks (EO via ethanol, CO via biomass gasification, and furan via known processes from cellulosic feedstocks).

11 Claims, 2 Drawing Sheets

(56) References Cited

U.S. PATENT DOCUMENTS

| | | | |
|---|---|---|---|
| 5,661,299 | A | 8/1997 | Purser |
| 6,852,865 | B2 | 2/2005 | Coates et al. |
| 2002/0028909 | A1 | 3/2002 | Kelsey et al. |
| 2009/0246430 | A1 | 10/2009 | Kriegel et al. |
| 2011/0262669 | A1 | 10/2011 | Kriegel et al. |
| 2014/0197580 | A1 | 7/2014 | Poulat |
| 2015/0126772 | A1 | 5/2015 | Cao et al. |

FOREIGN PATENT DOCUMENTS

| | | |
|---|---|---|
| WO | WO 2012/030619 | 3/2012 |
| WO | WO 2013/063191 | 5/2013 |
| WO | WO 2013/122905 | 8/2013 |
| WO | WO 2013/126375 | 8/2013 |
| WO | WO 2014/004858 | 1/2014 |
| WO | WO 2014/008232 | 1/2014 |

OTHER PUBLICATIONS

Vera, A. M. et al., "Synthesis and crystal structure of dimethyl-7-oxabicyclo[2.2,1] hept-5-ene exo,exo-2,3-clicarboxylate." Journal of Chemical Crystallography, 2007, vol. 37, pp. 543-548. See p. 544. Abstract Only.

Mahmoud, E. et al., "Production of benzoic acid from biomass-derived furan and methyl acrylate using lewis acidic zeolites," In Catalysis at the Confluence of Science and Technology, NAM24 Pittsburgh. PA, Jun. 15, 2015, pp. 1-2. See p. 1; and scheme 1.

Collias, D. I. et al., Biobased terephthalic acid technologies: I literature Review; Industrial Biotechnology, 2014, vol. 10, No. 2, p. 91-105, See whole document. Abstract Only.

Tachibana, Y. et al., "Synthesis and verification of biobased terephthaiic acid from furfural." Scientific Reports, Feb. 4, 2015 (Offline), vol. 5, article No. 8249 (5 internal pages) See p. 1, 2; and figure 1.

METHODS FOR PRODUCTION OF TEREPHTHALIC ACID FROM ETHYLENE OXIDE

CROSS REFERENCE TO RELATED APPLICATION

This application claims the benefit of U.S. Provisional Application 62/187,329 filed Jul. 1, 2015.

BACKGROUND OF THE INVENTION

Terephthalic acid (TPA) and its esters and derivatives are important precursors for the synthesis of polyesters and other useful materials.

The largest use of TPA at present is production of polyesters. For example, TPA is used to produce polyethylene terephthalate (PET) which is used extensively in consumer goods packaging, most prominently in the now ubiquitous plastic water bottles. TPA is produced on the scale of many millions of tons per year scale by oxidation of xylenes which are obtained from petroleum distillates.

There is strong demand from consumers and consumer goods companies for sustainable alternatives to petroleum-based plastics for packaging applications. Indeed, Coca Cola® and others have recently introduced PET containing biobased monoethylene glycol (MEG). Beverage bottles made from this PET are branded as the "Plant Bottle™" and have been well received in the marketplace. Unfortunately, since about 70% of the mass (and 80% of the carbon atoms) in PET derives from terephthalic and isophthalic acids, replacing petroleum-sourced MEG with biobased material yields PET that is only about 30% biobased and contains only 20% renewable carbon. There is huge interest in biobased IPA and TPA to enable fully biobased PET production, but to date no economically feasible biobased processes exist.

The present invention solves this problem and others related thereto.

SUMMARY OF THE INVENTION

The present invention addresses the problem that current biobased routes to terephthalic acid are carbon inefficient and expensive. The invention captures the recognition that terephthalic acid and related aromatic compounds can be accessed using ethylene oxide, carbon monoxide and furan as feedstocks. The process is characterized by high yields and high carbon efficiency. The process can utilize 100% biobased feedstocks (EO via ethanol, CO via biomass gasification, and furan via known processes from cellulosic feedstocks).

The inventive processes have advantages relative to other proposed processes for biobased aromatic diacids in terms of cost and carbon efficiency. The inventive processes provide unprecedented flexibility in terms of the manufacturer's ability to modulate the bio-content of the product: the terephthalic acid produced by the process can contain 0, 2, 4, 6, or 8 biomass-derived carbon atoms. This flexibility allows TPA producers to leverage various combinations of biobased and fossil-based feedstocks (e.g. chosen on best combination of availability, cost, or carbon footprint of each material) to provide the market with cost-effective low carbon footprint chemicals and polymers.

In a first aspect, the present invention provides novel processes for the production of terephthalic acid (TPA) and derivatives thereof using furan, ethylene oxide and carbon monoxide as feedstocks.

In a second aspect, the present invention provides novel processes for the production of terephthalic acid (TPA) and derivatives thereof using furan, ethanol, and carbon monoxide as feedstocks.

In certain embodiments, the invention provides processes for the integrated production of aromatic diacids from biomass, representative processes according to this embodiment include the steps of:
 a) treating biomass to produce ethanol;
 b) treating biomass to produce carbon monoxide;
 c) converting the ethanol to ethylene oxide;
 d) contacting ethylene oxide with the carbon monoxide in the presence of a catalyst to form succinic anhydride;
 e) oxidizing the succinic anhydride to provide a product selected from the group consisting of: maleic anhydride, maleic acid, fumaric acid, a mono- or di-ester of fumaric acid, a mono- or di-ester of maleic acid, a mono- or bis-salt of fumaric acid, a mono- or bis-salt of maleic acid, and a mixture of any two or more of these;
 f) contacting the product of step (e) with furan to provide a product containing a cyclohexene ring;
 g) dehydrating the cyclohexene ring-containing product to provide a compound selected from an aromatic acid anhydride, an aromatic diacid, a mono- or bis-salt of an aromatic diacid; a mono- or bis-ester of an aromatic diacid; and a mixture of any two or more of these.

DEFINITIONS

Figure 1:
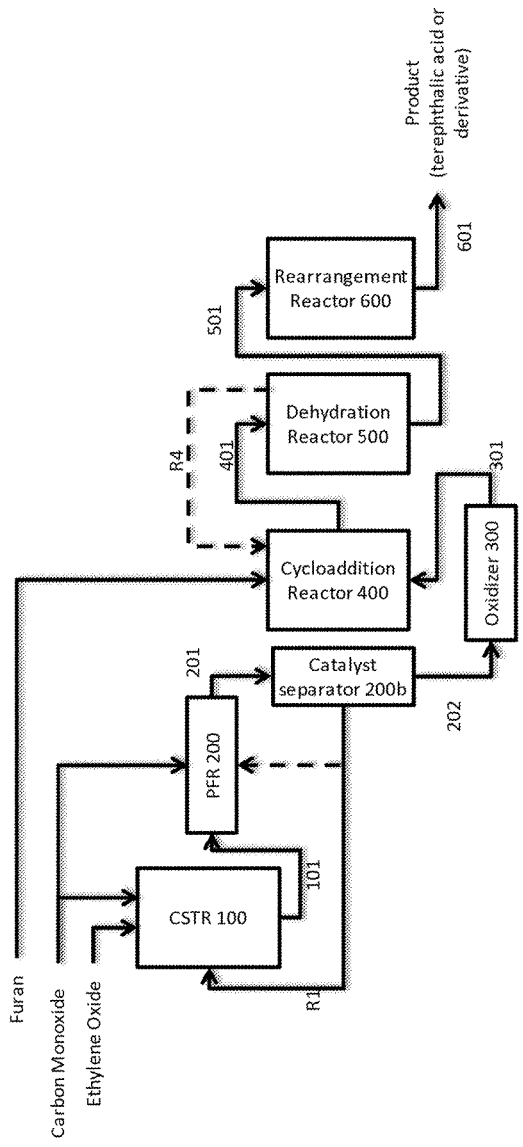
FIG. 1 is a flow diagram depicting various embodiments for the process arrangements of the invention.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March March's *Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of enantiomers or diastereomers are provided.

Furthermore, certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In some embodiments the compound is made up of at least about 95%, 97%, 98%, 99%, 99.5%, 99.7%, 99.8%, or 99.9% by weight of an enantiomer. In some embodiments the enantiomeric excess of provided compounds is at least about 90%, 95%, 97%, 98%, 99%, 99.5%, 99.7%, 99.8%, or 99.9%. In some embodiments, enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "hetercyclyl," "heterocycloaliphatic," or "heterocyclic" groups.

The term "epoxide", as used herein, refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "glycidyl", as used herein, refers to an oxirane substituted with a hydroxyl methyl group or a derivative thereof. The term glycidyl as used herein is meant to include moieties having additional substitution on one or more of the carbon atoms of the oxirane ring or on the methylene group of the hydroxymethyl moiety, examples of such substitution may include, but are not limited to: alkyl groups, halogen atoms, aryl groups etc. The terms glycidyl ester, glycidyl acrylate, glydidyl ether etc. denote substitution at the oxygen atom of the above-mentioned hydroxymethyl group, i.e. that oxygen atom is bonded to an acyl group, an acrylate group, or an alkyl group respectively.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer of the present invention is a copolymer, terpolymer, heteropolymer, block copolymer, or tapered heteropolymer of one or more epoxides.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include cyclopropane, cyclobutane, cyclopentane, cyclohexane, bicyclo[2,2,1]heptane, norbornene, phenyl, cyclohexene, naphthalene, spiro[4.5]decane.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; $-(CH_2)_{0-4}R°$; $-(CH_2)_{0-4}OR°$; $-O-(CH_2)_{0-4}C(O)OR°$; $-(CH_2)_{0-4}CH(OR°)_2$; $-(CH_2)_{0-4}SR°$; $-(CH_2)_{0-4}Ph$, which may be substituted with $R°$; $-(CH_2)_{0-4}O(CH_2)_{0-1}Ph$ which may be substituted with $R°$; $-CH=CHPh$, which may be substituted with $R°$; $-NO_2$; $-CN$; $-N_3$; $-(CH_2)_{0-4}N(R°)_2$; $-(CH_2)_{0-4}N(R°)C(O)R°$; $-N(R°)C(S)R°$; $-(CH_2)_{0-4}N(R°)C(O)NR°_2$; $-N(R°)C(S)NR°_2$; $-(CH_2)_{0-4}N(R°)C(O)OR°$; $-N(R°)N(R°)C(O)R°$; $-N(R°)N(R°)C(O)NR°_2$; $-N(R°)N(R°)C(O)OR°$; $-(CH_2)_{0-4}C(O)R°$; $-C(S)R°$; $-(CH_2)_{0-4}C(O)OR°$; $-(CH_2)_{0-4}C(O)N(R°)_2$; $-(CH_2)_{0-4}C(O)SR°$; $-(CH_2)_{0-4}C(O)OSiR°_3$; $-(CH_2)_{0-4}OC(O)R°$; $-OC(O)(CH_2)_{0-4}SR-$, $SC(S)SR°$; $-(CH_2)_{0-4}SC(O)R°$; $-(CH_2)_{0-4}C(O)NR°_2$; $-C(S)NR°_2$; $-C(S)SR°$; $-SC(S)SR°$; $-(CH_2)_{0-4}OC(O)NR°_2$; $-C(O)N(OR°)R°$; $-C(O)C(O)R°$; $-C(O)CH_2C(O)R°$; $-C(NOR°)R°$; $-(CH_2)_{0-4}SSR°$; $-(CH_2)_{0-4}S(O)_2R°$; $-(CH_2)_{0-4}S(O)_2OR°$; $-(CH_2)_{0-4}OS(O)_2R°$; $-S(O)_2NR°_2$; $-(CH_2)_{0-4}S(O)R°$; $-N(R°)S(O)_2NR°_2$; $-N(R°)S(O)_2R°$; $-N(OR°)R°$; $-C(NH)NR°_2$; $-P(O)_2R°$; $-P(O)R°_2$; $-OP(O)R°_2$; $-OP(O)(OR°)_2$; $SiR°_3$; $-(C_{1-4}$ straight or branched)alkylene)O—N(R°)_2$; or $-(C_{1-4}$ straight or branched)alkylene)C(O)O—N(R°)_2$, wherein each $R°$ may be substituted as defined below and is independently hydrogen, $C_{1-8}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur, or, notwithstanding the definition above, two independent occurrences of $R°$, taken together with their intervening atom(s), form a 3-12- or polycyclic ring having 0-4 heteroatoms independently selected from nitrogen, oxygen, and sulfur, which may be substituted as defined below.

Suitable monovalent substituents on $R°$ (or the ring formed by taking two independent occurrences of $R°$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-4}C(O)N(R°)_2$; $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R°$ include =O and =S.

Suitable divalent substituents on a saturated carbon atom of an "optionally substituted" group include the following: =O, =S, =NNR*_2, =NNHC(O)R*, =NNHC(O)OR*, =NNHS(O)_2R*, =NR*, =NOR*, $-O(C(R*_2))_{2-3}O-$, or $-S(C(R*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: $-O(CR*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of $R^\dagger$ are independently halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur.

As used herein, the term "catalyst" refers to a substance the presence of which increases the rate of a chemical reaction, while not being consumed or undergoing a permanent chemical change itself. As used herein, the term "about" preceding one or more numerical values means the numerical value ±5%.

DETAILED DESCRIPTION OF THE INVENTION

Processes

In one aspect, the present invention encompasses novel processes for the production of terephthalic acid and derivatives thereof.

In certain embodiments, the process utilizes ethylene oxide, furan and carbon monoxide as the feedstocks. In certain embodiments, the ethylene oxide is derived from ethanol via ethylene; therefore in another aspect, the present invention provides a process for the conversion of ethanol, carbon monoxide and furan into terephthalic acid and derivatives thereof. In certain embodiments, any one or more of the furan, the ethanol, or the carbon monoxide is derived from biomass.

In certain embodiments, the processes comprise reacting the ethylene oxide and carbon monoxide to form a four carbon product. In certain embodiments, the four carbon product is selected from the group consisting of succinic anhydride, succinic acid, a mono- or diester of succinic acid, a mono- or bis salt of succinic acid, and a mixture of two or more of these. In certain embodiments, the four carbon product comprises succinic anhydride. In certain embodiments, the four carbon product comprises succinic acid.

In certain embodiments, the processes include a step of converting this four carbon product to an unsaturated compound selected from the group consisting of: maleic anhydride, maleic acid, fumaric acid, a mono- or di-ester of fumaric acid, a mono- or di-ester of maleic acid, a mono- or his salt of maleic acid, a mono- or his salt of fumaric acid, and a mixture of any two or more of these.

In certain embodiments, the processes include a step of reacting the unsaturated compound from the previous step with the furan to provide an eight carbon product containing a cyclohexene ring.

It should be noted here that the term "an eight carbon product" as used in this specification refers to a product with eight carbon atoms joined to each other through carbon-carbon bonds—it should be understood that such a product may contain a total of more than eight carbon atoms if one includes carbon atoms separated from the eight carbon core by heteroatoms. For example, if the reactant in this step were the dibutyl ester of maleic acid, the eight carbon product might contain a total of sixteen carbon atoms: i.e. the eight carbon atoms in the disubstituted cyclohexene product core derived from the four carbon atoms in the furan and the four carbon atoms of the maleic moiety, plus eight additional carbon atoms in the form of the two butyl esters (if those esters remain intact through the process). The two butyl groups are separated from the eight carbon core by oxygen atoms and therefore are not counted in this example.

In certain embodiments, the processes include the step of dehydrating the eight carbon product containing a cyclohexene ring to form a product comprising a disubstituted benzene ring. In certain embodiments, the product comprising a disubstituted benzene ring is selected from the group consisting of phthalic anhydride, phthalic acid, a mono- or diester of phthalic acid, a mono- or bis-salt of phthalic acid, and a mixture of two or more of these.

In certain embodiments, the processes include the step of rearranging the product comprising a disubstituted benzene ring to provide a product selected from the group consisting of: terephthalic acid, a mono or diester of terephthalic aid, a mono or his metal salt of terephthalic acid; and a mixture of any two or more of these.

Therefore, in certain embodiments a process is provided for the conversion of ethylene oxide, furan and carbon monoxide to terephthalic acid or a derivative thereof, the process comprising the steps of:

a) reacting the ethylene oxide and carbon monoxide to form a four carbon product;

b) converting this four carbon product to an unsaturated compound selected from the group consisting of: maleic anhydride, maleic acid, fumaric acid, a mono- or di-ester of fumaric acid, a mono- or di-ester of maleic acid, a mono- or bis salt of maleic acid, a mono- or bis salt of fumaric acid, and a mixture of any two or more of these;

c) reacting the unsaturated compound from step (b) with the furan to provide an eight carbon product containing a cyclohexene ring;

d) dehydrating the eight carbon product containing a cyclohexene ring to form a product comprising a disubstituted benzene ring; and e) rearranging the product comprising a disubstituted benzene ring to provide a product selected from the group consisting of: terephthalic acid, a mono or diester of terephthalic aid, a mono or bis metal salt of terephthalic acid; and a mixture of any two or more of these.

In other embodiments, the present invention provides processes for the formation of terephthalic acid from ethanol, carbon monoxide and furan. These processes have the advantage of utilizing three operational feedstocks that are among the most abundant and efficiently produced of all biobased chemicals. As such the inventive processes have substantial advantages in terms of cost and overall carbon efficiency compared to alternative routes to biobased terephthalic acid.

In certain embodiments, a process is provided for the conversion of ethanol, carbon monoxide and furan to terephthalic acid, the process comprising the steps of:

a) reacting ethanol in a dehydration reactor to provide ethylene;

b) reacting the ethylene with oxygen to provide ethylene oxide;

c) reacting the ethylene oxide with carbon monoxide to provide a four carbon product;

d) converting this four carbon product to an unsaturated compound selected from the group consisting of: maleic anhydride, maleic acid, fumaric acid, a mono- or di-ester of fumaric acid, a mono- or di-ester of maleic acid, a mono- or bis salt of maleic acid, a mono- or bis salt of fumaric acid, and a mixture of any two or more of these;

e) reacting the unsaturated compound from step (b) with the furan to provide an eight carbon product containing a cyclohexene ring;

f) dehydrating the eight carbon product containing a cyclohexene ring to form a product comprising a disubstituted benzene ring; and g) rearranging the product comprising a disubstituted benzene ring to provide a product selected from the group consisting of: terephthalic acid, a mono or diester of terephthalic aid, a mono or bis metal salt of terephthalic acid; and a mixture of any two or more of these.

In certain embodiments of these processes, the four carbon product formed from the ethylene oxide and carbon monoxide comprises succinic anhydride. In certain embodiments, the succinic anhydride is formed from reaction of the ethylene oxide and two molar equivalents of carbon monoxide in the presence of a carbonylation catalyst. In certain embodiments, the ethylene oxide is reacted with a first molar equivalent of carbon monoxide to form a product comprising beta propiolactone and the beta propiolactone is subsequently reacted with a second equivalent of carbon monoxide to form succinic anhydride. In certain embodiments the two carbonylation steps are performed using the same carbonylation catalyst. In certain embodiments the two carbonylation steps are performed using two different carbonylation catalysts. Suitable carbonylation catalysts and process conditions for these processes are disclosed in U.S. Pat. No. 6,852,865 and in published PCT applications WO 2010118128, WO 2012030619, and WO 2013122905, the entire contents of each of which is incorporated herein by reference.

In certain embodiments, the reaction of ethylene oxide with carbon monoxide is catalyzed by a cobalt-based catalyst. In certain embodiments, the reaction of ethylene oxide with carbon monoxide is catalyzed by a catalyst comprising a cobalt carbonyl compound in combination with a Lewis acid. In certain embodiments the Lewis acid is a cationic metal-centered Lewis acid and the cobalt carbonyl is an anionic species.

In certain embodiments, the reaction of ethylene oxide with carbon monoxide is performed at a pressure from about 150 psi to about 3000 psi. In certain embodiments, the reaction pressure is between 200 psi and 1000 psi, between 400 and 800 psi, between 800 and 1200 psi, or between 1200 and 2000 psi.

In certain embodiments, the reaction of ethylene oxide with carbon monoxide is performed in a solvent. In certain embodiments, the solvent comprises an ether. In certain embodiments, the solvent is selected from the group consisting of 1,4-dioxane, tetrahydrofuran, glyme, diglyme, triglyme, and t-butyl methyl ether. In certain embodiments, the reaction of ethylene oxide with carbon monoxide is performed in a solvent comprising 1,4 dioxane. In certain embodiments, where the reaction of ethylene oxide with carbon monoxide is performed in two separate steps, the process utilizes different solvents for each step. In certain embodiments, the first carbonylation is performed in an ether-containing solvent and the second carbonylation is performed in hydrocarbon solvent.

In certain embodiments, the reaction of ethylene oxide with carbon monoxide is performed in a continuous process and a homogenous carbonylation catalyst is separated from the beta propiolactone and returned to the carbonylation reactor. In certain embodiments, the reaction of ethylene oxide with carbon monoxide is performed continuously in the presence of a heterogeneous carbonylation catalyst.

In certain embodiments of these processes, the step of converting the four carbon product to an unsaturated compound comprises an oxidation reaction. In certain embodiments, the step comprises an oxidative dehydrogenation reaction. In certain embodiments where the four carbon product comprises succinic anhydride, the oxidation process comprises a step of hydrolysis or alcoholysis of the succinic anhydride to provide succinic acid, a succinate ester, or a succinic acid salt which is then oxidized to provide an unsaturated product selected from the group consisting of: maleic anhydride, maleic acid, fumaric acid, a mono- or di-ester of fumaric acid, a mono- or di-ester of maleic acid, a mono- or bis salt of maleic acid, a mono- or bis salt of fumaric acid, and a mixture of any two or more of these. In certain embodiments, the step of oxidizing the four carbon product comprises heating. In certain embodiments, the step of oxidizing the four carbon product comprises contacting the four carbon product with a dehydrogenation catalyst. In certain embodiments, the step of oxidizing the four carbon product is performed in the presence of oxygen. In certain embodiments, the step of oxidizing the four carbon product is performed in the gas phase. In certain embodiments, the step of oxidizing the four carbon product is performed in the gas phase in the presence of air and a heterogeneous dehydrogenation catalyst.

In certain embodiments, the step of converting the four carbon product to an unsaturated compound comprises treating the four carbon compound with a transition metal-based catalyst. In certain embodiments, the step of converting the four carbon product to an unsaturated compound comprises treating the four carbon compound with an iron or molybdenum catalyst. In certain embodiments, the step of contacting is performed with the four carbon compound in the gas phase. In certain embodiments, the step of contacting is performed in the presence of air. In certain embodiments, the oxidizing step is performed under conditions wherein water is continuously removed from the reaction mixture.

In certain embodiments, the step of converting the four carbon product to an unsaturated compound is performed at a temperature between 100° C. and 300° C. In certain embodiments, the reaction zone is heated to a temperature between 100° C. and 200° C., between 120° C. and 180° C., between 150° C. and 220° C., or between 200° C. and 250° C.

In certain embodiments, the step of converting the four carbon product to an unsaturated compound comprises treating the four carbon compound with an acid catalyst. In certain embodiments, the oxidizing step comprises heating the compound in the presence of air and an acidic compound. In certain embodiments, the oxidizing step is performed under conditions wherein water is continuously removed from the reaction mixture.

In certain embodiments of these processes, the eight carbon product containing a cyclohexene ring formed from the reaction with furan comprises an oxo-bridged cyclohexene ring. In certain embodiments, the oxo-bridge is located between the two allylic carbons adjacent to the double bond in the cyclohexene ring (e.g. between ring carbons 3 and 6 if the double bond carbons are numbered 1 and 2). In certain embodiments, the eight carbon product further comprises two substituents at the homoallylic positions of the cyclohexene ring (e.g. the cyclohexene ring has substituents at carbons 4 and 5 if the double bond carbons are numbered 1 and 2). In certain embodiments, these homoallylic substituents are independently selected from the group consisting of: carboxy, carboxy ester, and carboxylate salt, or the two substituents may be taken together to form a cyclic acid anhydride.

In certain embodiments, the reaction of the furan with the unsaturated compound comprises a 2-plus-4 cycloaddition reaction. In certain embodiments, the cycloaddition reaction is promoted by heating a mixture of the furan and the unsaturated compound. In certain embodiments, the cycloaddition reaction is promoted by contacting a mixture of the furan and the unsaturated compound with a catalyst. In certain embodiments, the cycloaddition reaction is promoted by contacting a mixture of the furan and the unsaturated compound with a Lewis acid catalyst. In certain embodiments, the cycloaddition reaction is conducted in a solvent. In certain embodiments, the cycloaddition reaction is conducted in the gas phase. In certain embodiments, the cycloaddition reaction is conducted in the presence of a solid catalyst. In certain embodiments, the cycloaddition reaction is conducted in by heating a mixture of the furan and the unsaturated compound in the presence of a solid Lewis acid catalyst. In certain embodiments, the cycloaddition reaction is conducted in by heating a mixture of the furan and the unsaturated compound in a solvent in the presence of a solid Lewis acid catalyst. In certain embodiments, the cycloaddition step of comprises continuously flowing the mixture of furan and the unsaturated four carbon compound through a plug flow reactor containing a solid Lewis acid catalyst. In certain embodiments, the cycloaddition reaction is conducted in by heating a mixture of the furan and the unsaturated compound in a solvent in the presence of a homogeneous Lewis acid catalyst. In certain embodiments, the cycloaddition reaction is conducted in by heating a mixture of the furan and the unsaturated compound in a solvent in the presence of a homogeneous Lewis acid catalyst in a continuous stirred tank reactor. In certain embodiments, the cycloaddition reaction is conducted in by flowing a mixture of the furan and the unsaturated compound through a plug flow reactor in a solvent in the presence of a homogeneous Lewis acid catalyst. In certain embodiments, the cycloaddition reaction is conducted at a controlled temperature to retard the retro cycloaddition reaction. In certain embodiments, the cycloaddition reaction is conducted at a temperature below about 100° C. In certain embodiments, the cycloaddition reaction is conducted at a temperature below about 90° C., below about 80° C., below about 75° C., below about 70° C., below about 65° C., below about 60° C., below about 50° C., or below about 40° C.

In certain embodiments, the step of reacting furan with the unsaturated four carbon compound comprises heating a mixture of the furan and the unsaturated compound. In certain embodiments, the mixture is heated to a temperature between 50° C. and 300° C. In certain embodiments, the mixture is heated to a temperature between 50° C. and 150° C., between 100° C. and 200° C., between 120° C. and 180° C. or between 150° C. and 220° C.

In certain embodiments, the step of heating the mixture of the furan and the unsaturated four carbon compound comprises flowing the mixture through a heated plug flow reactor.

In certain embodiments, the cycloaddition reaction is conducted by flowing a mixture of the furan and the unsaturated compound through a heated plug flow reactor in a solvent in the absence of a catalyst. In certain embodiments, the mixture of unsaturated compound and furan is heated to a temperature between 50° C. and 300° C. In certain embodiments, the mixture is heated to a temperature between 50° C. and 150° C., between 100° C. and 200° C., between 120° C. and 180° C. or between 150° C. and 220° C. In certain embodiments, the step of heating the mixture of the furan and the unsaturated compound comprises flowing the mixture through a heated plug flow reactor. In certain embodiments, unreacted furan and/or unsaturated four carbon compounds are present in the outlet of the heated reactor. In certain embodiments, unreacted products present in the outlet of the reactor are separated from the cycloaddition product and recycled to the cycloaddition reactor inlet for further reaction.

In certain embodiments, the step of dehydrating the cyclohexene ring-containing compound comprises heating the cyclohexene compound in the presence of a dehydrating agent. In certain embodiments, the step includes continuously removing water vapor from a reaction zone where the dehydration reaction is performed. In certain embodiments, the dehydration reaction is acid catalyzed. In certain embodiments, the dehydration reaction is catalyzed by phosphoric or sulfuric acid. In certain embodiments, the dehydration reaction is acid catalyzed by a solid supported acid catalyst. In certain embodiments, the dehydration reaction is performed by heating the cyclohexene ring-containing compound in the presence of sulfuric acid. In certain embodiments where the cyclohexene ring-containing compound comprises a mono- or di-ester, the dehydration step results in hydrolysis of ester groups. In certain embodiments where the cyclohexene ring-containing compound comprises a mono- or di-ester, the dehydration conditions promote ester hydrolysis and the product is a diacid. In certain embodiments, where the cyclohexene ring-containing compound is a diacid, a mono-ester, or a di-ester, the dehydration step results in formation a cyclic anhydride.

In certain embodiments, the dehydration reaction is catalyzed by reaction with a strong base. In certain embodiments, where the cyclohexene compound comprises substituents that are esters or a cyclic anhydride, the dehydration reaction comprises treating the diester or anhydride with a strong base in the presence of water to provide a bis salt of an aromatic diacid. In certain embodiments, the bis salt comprises dipotassium phthalate. In certain embodiments, the dipotassium phthalate from the dehydration step is continuously fed to the rearrangement reaction.

In certain embodiments, where the cyclohexene compound comprises a substituent that is a carboxylate ester, the dehydration reaction comprises treating the ester with a strong base in the presence of water to form a salt of an aromatic acid. In certain embodiments, the salt formed comprises potassium phthalate. In certain embodiments, the potassium phthalate from the dehydration step is continuously fed to the rearrangement reaction. In certain embodiments, the alcohol liberated by the ester hydrolysis is recovered and recycled to an earlier step in the process.

In certain embodiments, the retro cycloaddition of the cyclohexene compound occurs to some extent during the dehydration reaction. Therefore, in certain embodiments, furan and/or the four carbon unsaturated compound are formed in the dehydration reactor and the process includes the step of recovering one or both of these materials and feeding them back to the cycloaddition reactor upstream. In this manner, the overall selectivity of the process can be kept high even where the selectivity in the dehydration step may not be optimal.

In certain embodiments, the dehydration reaction is catalyzed by contacting the cycloaddition product with dipotassium terephthalate in the presence of water. In certain embodiments, this process results in formation of terephthalic acid and dipotassium phthalate. In certain embodiments, the cycloaddition product is contacted with dipotassium terephthalate produced from the rearrangement reactor to which the cycloaddition product is fed, thereby providing a method to recycle the potassium salt used in the rearrangement reactor.

In certain embodiments, the product comprising a disubstituted benzene ring comprises an ortho substituted benzene ring. In certain embodiments, the ortho substituents of this product are independently selected from the group consisting of: carboxy, carboxy ester, and carboxylate salt or the two substituents may be taken together to form a cylclic acid anhydride.

In certain embodiments, the step of rearranging the disubstituted aromatic compound comprises treating a feed stream comprising one or more ortho disubstituted benzene compounds with a catalyst at elevated temperature to form a product mixture containing para substituted benzene compounds. In certain embodiments, the process includes the step of converting ortho disubstituted compounds in the feed stream to a bis phthalate salt. In certain embodiments, the ortho-substituted bis phthalate salt is contacted with a suitable catalyst to form a product stream containing para-substituted products. In certain embodiments, the step of contacting the ortho-substituted bis phthalate salt is performed at an elevated temperature. In certain embodiments, the step of contacting the ortho-substituted bis phthalate salt is performed at a temperature above about 200° C., above about 250° C., above about 300° C., above about 350° C. or above about 400° C. In certain embodiments, the step of rearranging the disubstituted aromatic compound is performed at elevated pressure. In certain embodiments, the step of rearranging the disubstituted aromatic compound is performed at elevated pressure under an atmosphere of $CO_2$.

In certain embodiments, the step of rearranging the disubstituted aromatic compound comprises continuously flowing a feed stream comprising one or more ortho disubstituted benzene compounds over a heterogenous a catalyst at elevated temperature to form a product mixture containing para substituted benzene compounds. In certain embodiments, the reaction zone is heated. In certain embodiments, the reaction zone is heated to a temperature between 100° C. and 500° C. In certain embodiments, the reaction zone is heated to a temperature between 100° C. and 200° C., between 120° C. and 180° C., between 150° C. and 220° C., between 200° C. and 300° C., or between 300° C. and 450° C.

In certain embodiments, the catalyst utilized for this transformation comprises a transition metal. In certain embodiments, the rearrangement is performed in the presence of a catalyst comprising a Group 10-12 transition metal. In certain embodiments, the rearrangement is performed in the presence of a catalyst comprising a Group 12 transition metal. In certain embodiments, the transformation is performed in the presence of a catalyst comprising cadmium. In certain embodiments, the transformation is performed in the presence of a catalyst comprising zinc. In certain embodiments, the transformation is performed in the presence of a catalyst comprising mercury.

In certain embodiments, the step of rearranging the disubstituted aromatic compound is performed at elevated pressure. In certain embodiments, the step of rearranging the disubstituted aromatic compound is performed at elevated pressure under an atmosphere of $CO_2$.

In certain embodiments, the process further includes continuously withdrawing a product stream containing terephthalic acid or an ester thereof from the rearrangement reaction zone. In certain embodiments, the process further includes a step of purifying the terephthalic acid (or esters thereof) withdrawn from the reaction zone. In certain embodiments, the purification includes distillation, crystallization, or a combination of both of these.

In certain embodiments, processes of the present invention are characterized in that they are continuous processes. In certain embodiments, such continuous processes are characterized in that two or more of the steps described above are combined and performed without isolation and purification of intermediate products or, in some cases, combined in a single operation or reactor.

In certain embodiments, the steps of oxidizing the four carbon compound and performing the cycloaddition reaction with furan are performed in a single reactor. In certain embodiments, the steps of performing the cycloaddition reaction and dehydrating the cycloaddition product are combined. In certain embodiments, the steps of dehydrating the cycloaddition product and rearranging the bis-substituted benzene product to terephthalic acid or a derivative thereof are combined.

In certain embodiments, processes of the present invention are characterized in that the terephthalic acid produced is biobased. Each of the three feedstocks may be derived from biobased feedstocks or derived from traditional fossil sources. One advantage of the present processes is the ability to independently select the source of each of the three feedstocks. For example, in certain parts of the world, furan (primarily derived from cellulosic waste is abundant) but access to biobased ethylene oxide is limited. In such regions the inventive processes described herein can be utilized to manufacture terephthalic acid with significant biocontent which is still cost-effective. Likewise, other regions may have abundant access to bio-sourced carbon monoxide (e.g. from gasification of biomass or municipal solid waste) but limited access to biobased ethylene oxide or furan.

In certain embodiments, the present invention is characterized by high carbon efficiency. The term carbon efficiency in this context refers to the fraction of carbon atoms in the primary process feedstocks (e.g. furan, ethylene oxide and carbon monoxide) that are incorporated into the final product (e.g. terephthalic acid). For example, if the process consumes 1 kg of ethylene oxide (containing 45.5 moles of carbon), 1.3 kg of carbon monoxide (containing 46.4 moles of carbon) and 1.8 kg of furan (containing 105.9 moles of carbon) to produce 3.3 kg of terephthalic acid (containing 159 moles of carbon), the carbon efficiency of the process would be calculated to be 80%.

In certain embodiments the present invention encompasses processes for the production of terephthalic acid from ethylene oxide, furan and carbon monoxide, characterized in that the carbon efficiency to terephthalic acid from the ethylene oxide, furan and carbon monoxide feedstocks is greater than 70%. In certain embodiments the processes of the present invention are characterized in that the carbon efficiency is greater than 75%, greater than 77%, greater than 78%, greater than 79%, greater than 80%, greater than 81%, greater than 82%, greater than 83%, greater than 84%, or greater than 85%.

In certain embodiments the present invention encompasses processes for the production of terephthalic acid from ethanol, furan and carbon monoxide, characterized in that the carbon efficiency to terephthalic acid from the ethanol, furan and carbon monoxide feedstocks is greater than 65%. In certain embodiments the processes of the present invention are characterized in that the carbon efficiency is greater than 67.5%, greater than 70%, greater than 75%, greater than 77%, greater than 78%, greater than 80%, greater than 81%, greater than 82%, greater than 83%, or greater than 85%.

EXAMPLES

The following non-limiting examples describe processes according to certain principles described herein.

Example 1

Continuous Process for Terephthalic Acid Production from Ethylene Oxide, Carbon Monoxide and Furan This example features a two stage continuous carbonylation process wherein the first carbonylation stage is operated at steady state in a continuous stirred tank reactor (CSTR) to produce a beta propiolactone stream and a second carbonylation stage where the beta propiolactone is converted to succinic anhydride in a plug flow reactor (PFR), with reference to FIG. 1:

A first carbonylation reaction zone comprising continuously stirred tank reactor CSTR 100 is fed with ethylene oxide and carbon monoxide. In the reactor, the ethylene oxide is contacted with carbon monoxide at superatmospheric pressure.

A first carbonylation product stream 101 comprising beta propiolactone, solvent, dissolved carbonylation catalyst and a fraction of unreacted ethylene oxide is taken from CSTR 100 and directed to a second carbonylation reaction zone, consisting of plug flow reactor PFR 200. PFR 200 is fed with additional CO and operated at a temperature and pressure sufficient to convert the residual ethylene oxide to beta propiolactone and all the beta propiolactone to succinic anhydride.

A crude succinic anhydride product stream 201 is taken from the second carbonylation reaction zone and directed to catalyst separator 200b consisting of precipitation/filtration unit where solid succinic anhydride is separated from the carbonylation catalyst and the solvent to provide a purified succinic anhydride stream 202 containing of succinic anhydride and a recycling stream R1 containing catalyst and solvent which are returned to the inlet of CSTR 100.

The purified succinic anhydride product stream 202 is continuously fed to Oxidizer 300 where it is oxidized. In Oxidizer 300 the succinic anhydride is vaporized into a stream of heated air and flowed rapidly through a catalyst bed containing a solid iron-based dehydrogenation catalyst. Maleic anhydride stream 301 is obtained at the exit of the catalyst bed.

The maleic anhydride stream 301 is optionally diluted with solvent and combined with furan in a 1:1 mol ratio in Cycloaddition Reactor 400. In reactor 400, the furan and maleic anhydride react over a solid-supported Lewis acid catalyst (for example a tin or zirconium based molecular sieve-supported catalyst) to form a cycloaddition product. Reactor 400 is operated at a temperature below about 80° C. to prevent retro cycloaddition reactions. Product stream 401 exiting the cycloaddition reactor contains the cyclohexene compound 7-oxabicyclo[2.2.1]hept-5-enecis-2,3-dicarboxylic anhydride.

Product stream 401 is continuously fed to Dehydration Reactor 500 where the 7-oxabicyclo[2.2.1]hept-5-enecis-2,3-dicarboxylic anhydride contained in stream 401 is converted to the his substituted benzene product phthalic anhydride which exits via product stream 501.

Stream 501 is fed to Rearrangement Reactor 600 where at least a portion of the phthalic anhydride in stream 501 is converted to terephthalic acid or derivatives thereof. In Rearrangement Reactor 600 stream 501 is contacted with potassium hydroxide to form dipotassium phthalate which is then contacted at elevated temperature with a cadmium-containing catalyst. Stream 601 exiting Rearrangement Reactor 600 is treated to recover the desired terephthalic acid via product stream 601.

Example 1a

The process of Example 1a is operated according to the principles described above in Example 1 except the catalyst separator unit 200b comprises a nanofiltration unit. In this example, the succinic anhydride stream fed to oxidizer 300 contains solvent.

Example 1b

The process of Example 1b is operated according to the principles described above in Example 1 except the succinic anhydride is reacted with water in stream 202 which then contains succinic acid. In a related example, stream 202 contains succinic anhydride, but oxidizer 300 is co-fed with water such that succinic acid is formed as an intermediate during the conversion in reactor 300.

Example 1c

The process of Example 1c is operated according to the principles described above in Example 1 except the maleic anhydride stream 301 is rectified to separate unreacted succinic anhydride which is returned to the inlet of Oxidizer 300 for further conversion.

Example 2

A continuous process for terephthalic acid production from ethanol, carbon monoxide and furan.

Figure 2:
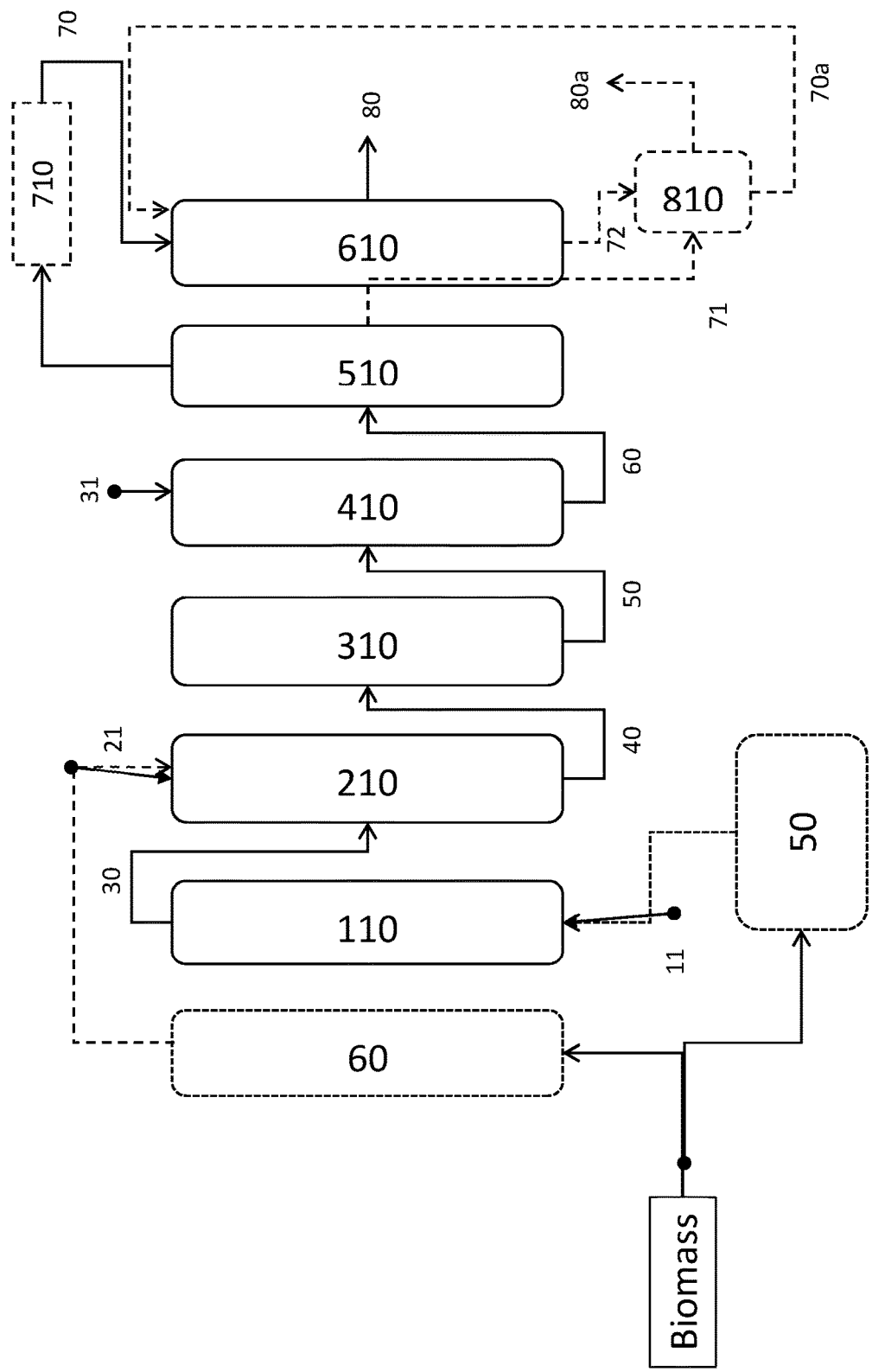
FIG. 2 is a flow diagram depicting additional embodiments for the process arrangement of the invention.

This example features a two stage continuous carbonylation process wherein the ethanol, carbon monoxide and furan are the operational feedstocks. An alternative embodiment of this process utilizes biomass as the primary input to generate ethanol (e.g. via fermentation) and carbon monoxide (e.g. via gasification of fermentation residue). Though not shown, the furan could, in principle be derived from the same biomass source. With reference to FIG. 2:

Ethylene oxide production unit 110 is fed with ethanol via input 11. Ethylene oxide production unit 110 operates according to known principles to first dehydrate the ethanol to ethylene, which is then converted to ethylene oxide in a separate step. Ethylene oxide exits unit 110 via stream 30. The ethanol is optionally fed to the ethylene oxide unit 110 from fermentor 50 which is fed from a biomass source (e.g. sugar or cellulosic feedstock).

Ethylene oxide stream 30 is fed to carbonylation reactor 210 along with carbon monoxide stream 21 (optionally derived from biomass via gasifier 60) in reactor 210, a carbonylation catalyst promotes the reaction of two equivalents of carbon monoxide in a continuous plug flow reaction format to provide a succinic anhydride which exits reactor 210 in stream 40.

Succinic anhydride in stream 40 is directed to oxidation reactor 310 where it is oxidized over a dehydrogenation catalyst in the presence of air to provide maleic anhydride which exits via product stream 50.

Product stream 50 is diluted with solvent and combined with furan from stream 31 in reactor 410. In reactor 410 the furan and reacts with the maleic anhydride via 2+4 cylcoaddition to provide 7-oxabicyclo[2.2.1]hept-5-enecis-2,3-dicarboxylic anhydride which is taken from the reactor in product stream 60.

Stream 60 is fed to reactor 510 where the compound is treated under dehydrating conditions to produce phthalic anhydride and water. The phthalic anhydride is optionally stored at tank 710 where it can be utilized for other purposes.

Phthalic anhydride stream 70 is fed to rearrangement unit 610 where it is converted to the bis potassium salt of phthalic acid and treated with a rearrangement catalyst to provide dipotassium terephthalate, the dipotassium terephthalate is then converted to terephthalic acid.

Optionally, potassium terephthalate is taken from unit 610 via stream 72. Stream 72 is directed to reactor 810 where it is contacted in the presence of water with phthalic anhydride taken from reactor 510 via stream 71. After reaction in 810, stream 70a containing the bis potassium salt of phthalic acid is fed to tehe inlet of reactor 610 for rearrangement to dipotassium terephthalate, while the terephthalic acid exits via stream 80a. In this way the potassium used in unit 610 is recycled.

Example 2a

The process of Example 2a is operated according to the principles described above in Example 2 except the Carbonylation reactor 210 comprises a combination of a CSTR 100 and PFR 200. In the CSTR 100, the ethylene oxide reacts with one molecule of carbon monoxide to form beta propiolactone which is fed to the PFR 200 for further reaction to form succinic anhydride.

Example 2b

The process of Example 2b is operated according to the principles described above in Example 2 except the succinic anhydride is reacted with water in stream 40 which then contains succinic acid. In a related example, stream 40 contains succinic anhydride, but reactor 310 is fed with water such that succinic acid is formed as an intermediate during the conversion in reactor 310.

Example 2c

The process of Example 2c is operated according to the principles described above in Example 2 except the succinic anhydride is converted to a mixture of maleic acid and fumaric acid in oxidation reactor 310.

The fumaric/maleic acid stream 50 is fed to cycloaddition reactor 410 where it is contacted with furan from feed stream 31 and converted to 7-oxabicyclo[2.2.1]hept-5-enecis-2,3-dicarboxylic acid which exits via stream 60 to dehydration reactor 510. In this example, the product exiting reactor 510 via stream 70 is phthalic acid. The phthalic acid stream is converted in rearrangement unit 610 to terephthalic acid.

Example 2d

The process of Example 2d is operated according to the principles described above in Example 2 except cycloaddition reactor 410 and dehydration reactor 510 are combined into one unit. In this Example the combined cycloaddition/dehydration reactor is operated with dual catalyst zones: a first catalyst zone containing a catalyst that promotes 2+4 cylcoaddition and a second catalyst zone containing a catalyst that promotes dehydration of -oxabicyclo[2.2.1]hept-5-enecis-2,3-dicarboxylic anhydride to phthalic anhydride. A degree of retro 2+4 cycloaddition occurs in the second catalyst zone such that the intermediate product stream from that zone contains a mixture of phthalic anhydride, maleic anhydride and furan. The phthalic anhydride is separated from the maleic anhydride and furan which are returned to the first catalyst zone for reconversion.

Example 2e

The process of Example 2e is operated according to the principles described above in Example 2 except reactor 410 contains a solid-supported Lewis acid catalyst (for example a tin or zirconium based molecular sieve-supported catalyst) and reactor 410 is operated at a temperature below about 80° C. to prevent retro cycloaddition reactions.

Other Embodiments

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A process for making a chemical product comprising an aromatic diacid or derivative thereof comprising the steps of:
   a) treating biomass to produce ethanol;
   b) treating biomass to produce carbon monoxide;
   c) converting the ethanol to ethylene oxide;
   d) contacting ethylene oxide with the carbon monoxide in the presence of a catalyst to form succinic anhydride;
   e) oxidizing the succinic anhydride to provide a compound selected from the group consisting of: maleic anhydride, maleic acid, fumaric acid, a mono- or di-ester of fumaric acid, a mono- or di-ester of maleic acid, a mono- or bis-salt of fumaric acid, a mono- or bis-salt of maleic acid, and a mixture of any two or more of these;
   f) contacting the compound of step (e) with furan to provide a compound containing a cyclohexene ring;
   g) dehydrating the compound containing the cyclohexene ring to provide at least one of an aromatic acid anhydride, an aromatic diacid, a mono- or bis-salt of an aromatic diacid; and a mono- or bis-ester of an aromatic diacid as the chemical product.

2. The process of claim 1, wherein at least one compound provided by oxidizing the succinic anhydride is maleic anhydride.

3. The process of claim 1, wherein at least one compound provided by dehydrating the cylcohexene ring is phthalic anhydride.

4. The process of claim 1, further comprising the step of converting the chemical product of step (g) to at least one of terephthalic acid, a mono- or di-ester of terephthalic aid, a mono- or bis-metal salt of terephthalic acid.

5. The process of claim 1, wherein the step of oxidizing the succinic anhydride is performed in a continuous flow reactor.

6. The process of claim 5, wherein the step of oxidizing the succinic anhydride is performed over a solid catalyst.

7. The process of claim 1, wherein the step of contacting the compound of step (e) with furan is performed in a continuous flow reactor.

8. The process of claim 7, wherein the step of contacting the compound of step (e) with furan is performed over a solid catalyst.

9. The process of claim 1, wherein the carbon monoxide is derived from biomass gasification.

10. The process of claim 1, wherein the furan is derived from a biobased feedstock.

11. The process of claim 1, characterized in that a carbon efficiency of the process is greater than 80% where carbon efficiency is calculated by: determining the number of carbon atoms contained in a mass of aromatic diacid produced by the process, dividing that number of carbon atoms by the total number of carbon atoms fed to the process in the form of ethanol, carbon monoxide and furan to produce that mass of aromatic diacid.

* * * * *